US012616495B2

(12) United States Patent
Kase et al.

(10) Patent No.: US 12,616,495 B2
(45) Date of Patent: May 5, 2026

(54) TREATMENT TOOL AND METHOD OF PRODUCING TREATMENT TOOL

(71) Applicant: OLYMPUS MEDICAL SYSTEMS CORP., Tokyo (JP)

(72) Inventors: Seigo Kase, Sagamihara (JP); Takashi Nagata, Nagano (JP); Yusuke Inui, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 770 days.

(21) Appl. No.: 17/891,280

(22) Filed: Aug. 19, 2022

(65) Prior Publication Data

US 2023/0070359 A1     Mar. 9, 2023

Related U.S. Application Data

(60) Provisional application No. 63/241,150, filed on Sep. 7, 2021.

(51) Int. Cl.
　　*A61B 17/32*　　　(2006.01)
　　*A61B 17/00*　　　(2006.01)
　　*A61B 17/28*　　　(2006.01)
(52) U.S. Cl.
　　CPC .. *A61B 17/320092* (2013.01); *A61B 17/2841* (2013.01); *A61B 2017/00526* (2013.01); *A61B 2017/320094* (2017.08)
(58) Field of Classification Search
　　CPC ............ A61B 17/2816; A61B 17/2841; A61B 17/2909; A61B 17/320092;

(Continued)

(56) References Cited

U.S. PATENT DOCUMENTS 5,722,284 A * 3/1998 Linsmeyer ............ B25B 27/146
　　　　　　　　　　　　　　　　　　72/409.14
6,139,561 A 10/2000 Shibata et al.
(Continued)

FOREIGN PATENT DOCUMENTS

CN　　103747752 A　　4/2014
EP　　　2436330 A1 *　4/2012　............. A61B 17/28
(Continued)

OTHER PUBLICATIONS

Office Action dated Nov. 4, 2025, issued in corresponding Chinese Patent Application No. 202211084358.8.

*Primary Examiner* — Kankindi Rwego
(74) *Attorney, Agent, or Firm* — Morgan, Lewis & Bockius LLP

(57) ABSTRACT

Treatment tool includes a fixed handle, a shaft extending distally from the fixed handle, a treatment portion projecting distally from the shaft and configured to treat biological tissue, a jaw pivotably rotatably with respect to the shaft and, with the treatment portion, configured to grasp the biological tissue therebetween, a movable handle extending proximally from the jaw and causing the jaw to open and close relative to the treatment portion by proximally approaching or separating from the fixed handle, and a first adjusting member provided on the movable handle and having an extension protruding toward the fixed handle and, when the movable handle is brought into close proximity to the fixed handle, abutting the fixed handle. Changing the amount (length) by which the extension of the first adjusting member protrudes from the movable handle, adjusts an amount of the stroke of the movable range of the movable handle.

19 Claims, 13 Drawing Sheets

(58) Field of Classification Search
CPC ........... A61B 2017/00526; A61B 2017/00725;
A61B 2017/320094; A61B 90/06; B25B
7/18; B25B 7/22; B26B 17/02
USPC ......................................................... 606/169
See application file for complete search history.

(56) References Cited

U.S. PATENT DOCUMENTS

| | | | |
|---|---|---|---|
| 6,569,178 B1 | 5/2003 | Miyawaki et al. | |
| 8,974,447 B2 | 3/2015 | Kimball et al. | |
| 2004/0193199 A1* | 9/2004 | Hashiguchi | A61B 17/320092 |
| | | | 606/169 |
| 2007/0191713 A1* | 8/2007 | Eichmann | A61B 17/1606 |
| | | | 600/471 |
| 2012/0060376 A1* | 3/2012 | Polofsky | B25B 7/18 |
| | | | 30/177 |
| 2012/0245582 A1* | 9/2012 | Kimball | A61B 17/320092 |
| | | | 606/41 |
| 2015/0080925 A1* | 3/2015 | Schulte | A61B 17/285 |
| | | | 606/169 |
| 2016/0183964 A1 | 6/2016 | Katsumata | |
| 2017/0105756 A1 | 4/2017 | Katsumata | |
| 2018/0117365 A1 | 5/2018 | Kase | |
| 2019/0167288 A1 | 6/2019 | Schulte et al. | |
| 2019/0307503 A1 | 10/2019 | Katsumata | |

FOREIGN PATENT DOCUMENTS

| | | |
|---|---|---|
| JP | 2000-000249 A | 1/2000 |
| JP | 2007-037568 A | 2/2007 |
| WO | 2015/159600 A1 | 10/2015 |
| WO | 2016/204046 A1 | 12/2016 |

* cited by examiner

TREATMENT TOOL AND METHOD OF PRODUCING TREATMENT TOOL

RELATED APPLICATION DATA

This application is based on and claims priority under 35 U.S.C. § 119 to U.S. Provisional Application No. 63/241, 150 filed on Sep. 7, 2021, the entire contents of which are incorporated herein by reference.

FIELD OF THE INVENTION

The present invention relates to a treatment tool and a method of manufacturing a treatment tool.

DESCRIPTION OF THE RELATED ART

Conventionally, a treatment tool for treating a biological tissue by imparting treatment energy to a biological tissue is known (see, for example, Patent Document 1). In the treatment tool described in Patent Document 1, by gripping the grip portion and the arm body, the biological tissue is grasped between the clamp body and the probe portion.
Prior art documents—Patent Document 1: JP 2000-000249.

SUMMARY OF THE INVENTION

Problem to be Solved by the Invention

In the treatment tool, the amount of gripping force for grasping the biological tissue is such that a variation occurs due to the differences between each individual treatment tool. Therefore, there has been a demand for a technique capable of adjusting the amount of grasping force and stably grasping a biological tissue.

In view of the above, it is an object of the present invention to provide a treatment tool capable of stably grasping a biological tissue, and a method of manufacturing a treatment tool.

Means for Solving the Problem

In order to solve the above problems and to achieve the purpose, a treatment tool according to the present invention includes a fixed handle, a shaft extending distally from the fixed handle, a treatment portion projecting distally from the shaft and configured for treating a biological tissue, a jaw rotatably provided with respect to the shaft and configured for grasping the biological tissue, a movable handle extending proximally from the jaw and causing the jaw to open or close, and a first adjusting member including a protrusion, the first adjusting member extending from one of the fixed handle and the movable handle toward the other handle and the first adjusting member abutting against the other handle when the movable handle is brought into proximity with respect to the fixing handle. By changing a length of the protrusion or a position of the protrusion, it is possible to adjust the movable range of the movable handle, i.e., the stroke of the movable handle.

A treatment tool according to the present invention comprises a fixed handle, a shaft extending distally from the fixed handle, a treatment portion projecting distally from the shaft and configured for treating biological tissue, a jaw rotatably provided with respect to the shaft and configured for grasping the biological tissue between the treatment portion, a movable handle extending proximally from the jaw and causing the jaw to open and close, and a second adjusting member provided inside at least one of the jaw and the movable handle to adjust a rigidity thereof.

A method of manufacturing a treatment tool according to the present invention includes a step of measuring an initial amount of a gripping force between a treatment portion and a jaw when a fixed handle and a movable handle are gripped, and a step of adjusting the initial amount of the gripping force to a second gripping force amount by one of both of the first adjusting member and the second adjusting member.

Effect of the Invention

According to the treatment tool and the method of manufacturing the treatment tool according to the present invention, it is possible to stably grasp the biological tissue.

BRIEF DESCRIPTION OF THE DRAWINGS

FIG. 10C is a diagram illustrating a configuration of a second adjusting member according to the fifth embodiment.

DETAILED DESCRIPTION OF THE PREFERRED EMBODIMENT(S)

Modes for Carrying Out the Invention

Figure 1:
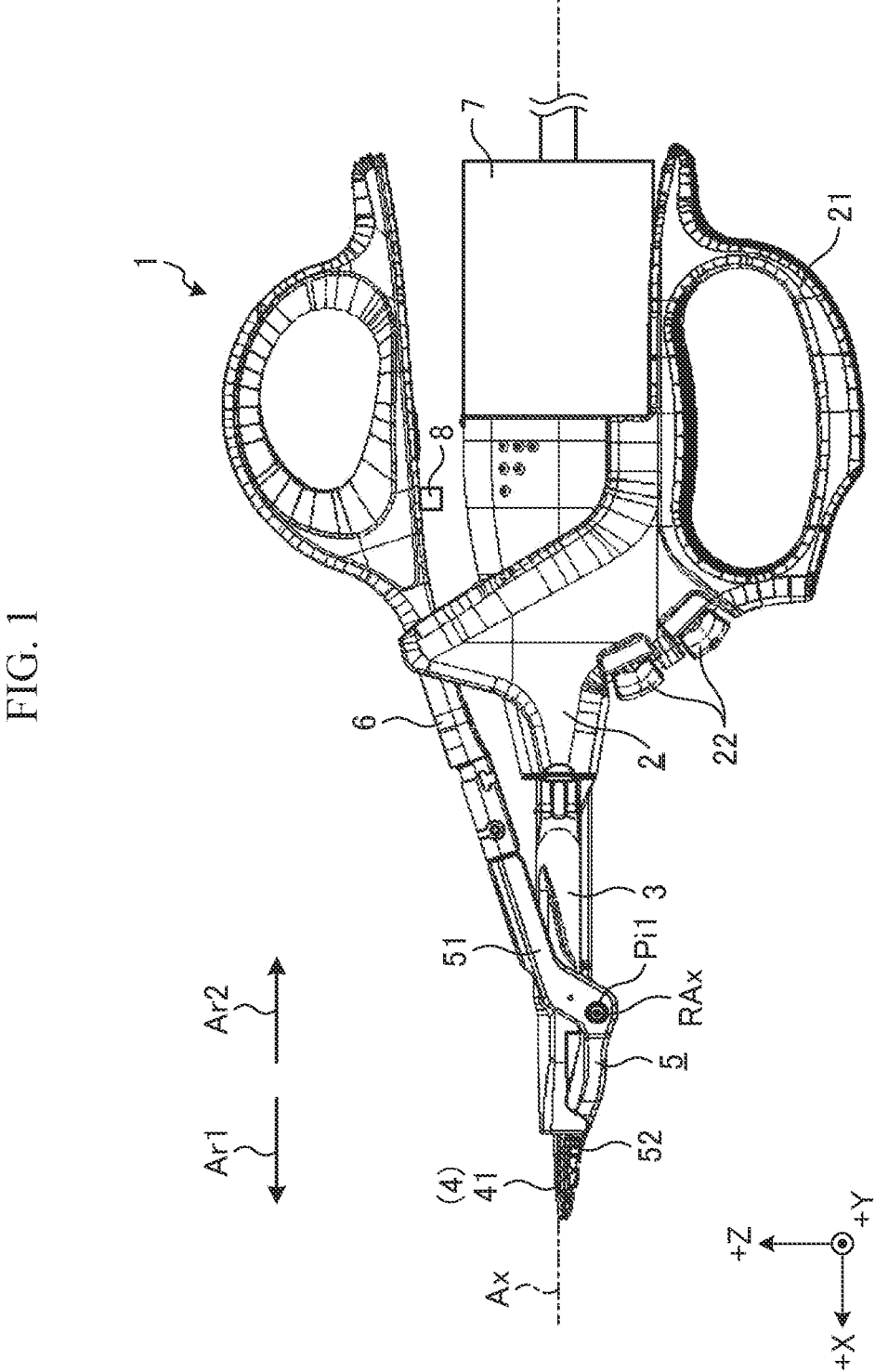
FIG. 1 is a view showing a treatment instrument according to the first embodiment.

Hereinafter, embodiments for carrying out the present invention (hereinafter, embodiments) will be described with reference to the accompanying drawings. However, the present invention is not limited by the embodiments described below. In addition, in the description of the drawings, the same parts are denoted by the same reference numerals.

First Embodiment

Schematic of the Procedure Device

FIG. 1 is a view showing a treatment tool 1 according to the first embodiment. In the following, in describing the configuration of the treatment tool 1, the X-axis, Y-axis, and Z-axis are mutually orthogonal, as shown by the XYZ coordinate axis in FIG. 1. The X-axis is an axis parallel to the central axis Ax of the shaft 3 (FIG. 1), the Y-axis is an axis perpendicular to the plane of the paper, and the Z-axis is an axis along the vertical direction of FIG. 1. In addition, in the following, one side along the central axis Ax (+X-axis side) is described as a distal end side Ar1, and the other side (–X-axis side) is described as a proximal end side Ar2, where arrow Ar1 indicates a distal direction and arrow Ar2 indicates a proximal direction.

The treatment tool 1 treats the target site by imparting treatment energy to a site to be treated in a biological tissue (hereinafter, described as a target site). Here, the procedure energy is, for example, ultrasonic energy and radiofrequency energy, but embodiments can include other procedure energies, such as thermal energy (heat energy). Also, such treatment means, for example, coagulation (sealing) of a target site, incision of a target site, but other treatment operations can be conducted with the treatment tool, such as grasping, exfoliating, and incising.

In the first embodiment, the treatment tool 1 is a treatment instrument of a forceps type. The treatment tool 1 includes, as shown in FIG. 1, a fixed handle 2, a shaft 3, a vibration transmission member 4, a jaw 5, a movable handle 6, an ultrasonic transducer 7, and a first adjusting member 8.

As shown in FIG. 1, the fixed handle 2 includes a handle body 21 and one or more switches 22. The handle body 21 is a portion held by an operator such as a medical professional. The one or more switches 22 are provided such that a portion is exposed to the outside from the side surface of the distal end-side Ar1 of the fixed handle 2. The one or more switches 22 are operable by an operator to initiate a treatment operation that imparts treatment energy to the site of interest, such as by outputting an operation signal corresponding to the output start operation to the control device electrically connected to the treatment tool 1 (not shown).

Shaft 3 has a generally cylindrical shape. The end portion of the proximal end side Ar2 of the shaft 3 is attached to the end portion of the distal end side Ar1 of the fixed handle 2. That is, the shaft 3 extends toward the distal end-side Ar1 from the fixed handle 2.

Vibration transmission member 4 has a long shape and is composed of a conductive material. Further and as shown in FIG. 1, the vibration transmission member 4 includes a treatment portion 41, which is inserted into the shaft 3 while an end portion of the distal end-side Ar1 is exposed to the outside. The proximal end side Ar2 of the vibration transmission member 4 is operatively connected to the ultrasonic transducer 7, which can be constituted by a bolt-clamped Langevin transducer (BLT). The vibration transmission member 4 transmits the ultrasonic vibration generated by the BLT from the proximal end side Ar2 to the treatment portion 41. In the first embodiment, the ultrasonic vibration is a longitudinal vibration vibrating in a direction along the central axis Ax. By the longitudinal vibration, the treatment portion 41 vibrates at a desired amplitude.

Figure 2:
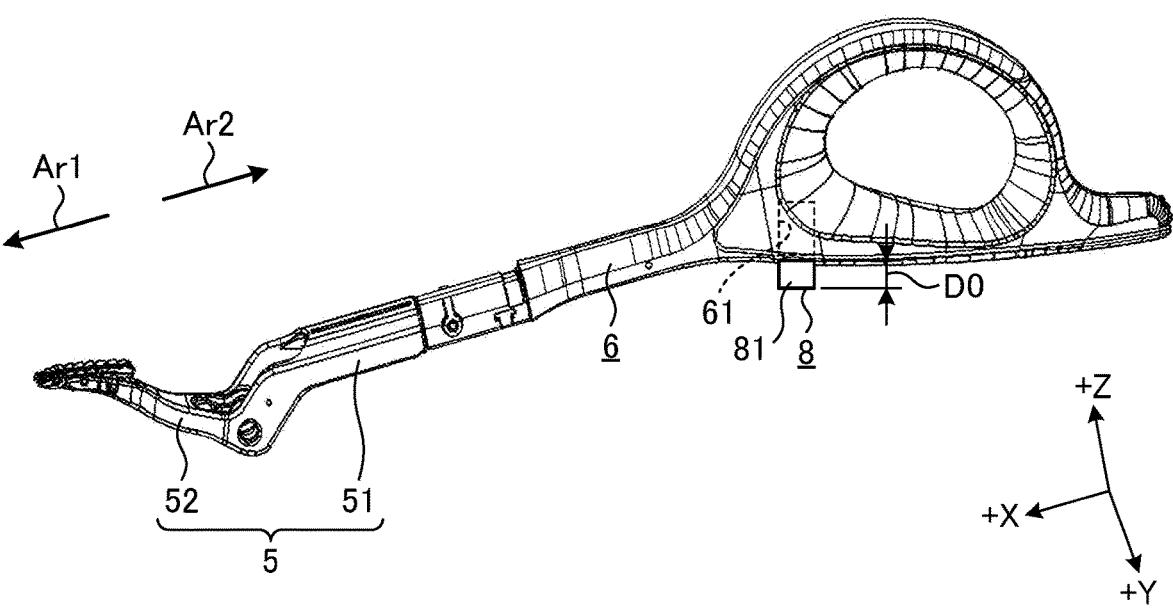
FIG. 2 is a diagram illustrating a configuration of the first adjusting member.

The jaw 5 is pivotally supported with respect to the shaft 3 by a cylindrical pin Pi1 (FIG. 1). In the following, for convenience of illustration, the central axis of the pin Pi1 is described as the rotation axis RAx. Here, the rotation axis RAx is located on the –Z-axis side with respect to the central axis Ax (in FIG. 1, the lower side) as well as located perpendicular to a plane including the central axis Ax. The jaw 5 includes a connecting portion 51 and a grip portion 52 as shown in FIG. 2. The end of the connecting portion 51 toward the distal end side Ar1 is pivotally supported relative to the shaft 3 by a pin Pi1. Further, the connecting portion 51 extends from the pivotally supported location at pin Pi1 at the distal end side Ar1 toward the +Z-axis side (in FIG. 1, the upper side) and toward the proximal end side Ar2 and portions of the connecting portion 51 are positioned on the +Z-axis side with respect to the shaft 3 and the fixed handle 2. The grip portion 52 is a portion which extends from the distal end side Ar1 of the connecting portion 51 toward the distal end side Ar1 and is positioned on the –Z axis side with respect to the shaft 3, and is configured to cooperate with the treatment portion 41 to grasp the target portion. In the first embodiment, the jaw 5 is made of a metal material, but the jaw 5 is not limited to a metal material and may be made of other materials.

The movable handle 6 is a portion which accepts an opening/closing control by an operator. The movable handle 6 has an elongated shape and the end of the distal end side Ar1 is connected to the end of the proximal end side Ar2 at the connecting portion 51. That is, the movable handle 6 extends from the jaw 5 toward the proximal end side Ar2. The movable handle 6 is rotatable about the rotation axis RAx together with the jaw 5 in response to an opening/closing control by an operator, by which the movable handle 6 is brought into close proximity to or separated from the fixed handle 2. Thus, the grip portion 52 opens and closes with respect to the treatment portion 41. In the first embodiment, the movable handle 6 is made of a resin material, but the movable handle 6 is not limited to a resin material, and may be made of other materials.

The ultrasonic transducer 7 is detachably connected to the end of the proximal end side Ar2 in the fixed handle 2. The ultrasonic transducer 7, although not shown specifically, comprises a BLT for generating ultrasonic vibration in response to the supply of driving power.

The first adjusting member 8 adjusts the range of movement of the movable handle 6, i.e., the movement by which the movable handle 6 is brought into close proximity to or separated from the fixed handle 2, which is the stroke of the movable handle 6. Note that the detailed configuration and function of the first adjusting member 8 will be described in the "configuration of the first adjusting member" and the "function of the first adjusting member" described later, respectively.

The treatment tool 1 described above operates as shown below. The operator holds the treatment tool 1 by hand and inserts the distal end portion of the treatment tool 1 into a body cavity, such as a peritoneal cavity. Then, the operator operates the movable handle 6 and opens and closes the grip portion 52 with respect to the procedure portion 41, thereby grasping the target site between the treatment portion 41 and the grip portion 52. After this, the operator performs an output start operation on the switch 22. Then, a control device (not shown) electrically connected to the treatment tool 1 imparts treatment energy to the target site grasped between the treatment portion 41 and the grip section 52 in response to an operation signal corresponding to an output start operation from the switch 22. That is, the control device treats the subject site.

For example, when applying ultrasonic energy to a site of interest, the control device provides a driving power to the BLT constituting the ultrasonic transducer 7. Thus, the BLT generates a longitudinal vibration (ultrasonic vibration), which vibrates in a direction along the central axis Ax. Further, the treatment portion 41, by the longitudinal vibration, vibrates at a desired amplitude. Then, ultrasonic vibration is applied from the treatment portion 41 to the target site grasped between the treatment portion 41 and the grip portion 52. In other words, ultrasonic energy is applied from the treatment portion 41 to the target site.

Further, for example, when imparting high-frequency energy to the target site, the controller supplies high-frequency power between the jaw 5 and the vibration transmission member 4. Thus, a high frequency current flows through the target site grasped between the treatment portion 41 and the grip portion 52. In other words, the subject site is imparted with high frequency energy.

Configuration of the First Adjusting Member

Next, a configuration of the first adjusting member 8 will be described. FIG. 2 is a diagram illustrating a configuration of the first adjusting member 8. The first adjusting member 8 is provided on the movable handle 6 and extends from the surface of the movable handle 6 toward the fixed handle 2. The first adjusting member 8 has a protruding portion 81 (FIG. 2) which abuts on the fixed handle 2 when the movable handle 6 is brought into close proximity to the fixed handle 2.

In the first embodiment, the first adjusting member 8 is constituted by a screw member, such as a set screw, screwed into the inner surface of the recess 61 provided in the movable handle 6 (FIG. 2). By the first adjusting member 8, by changing the screwed state with respect to the inner surface of the recess 61, the amount D0 by which the protruding portion 81 (FIG. 2) extends from the surface of the movable handle 6, i.e., the length of the protruding portion 81, can be adjusted. In other words, the screw member can be threaded into the recess such that the protruding portion 81 is shorter or longer. The first adjusting member 8 is not limited to a screw member, as long as the amount D0 of the protruding portion 81 can be adjusted to any amount (for example, commensurate with the overall length of the first adjusting member 8 and considering the rigidity of the movable handle and jaws, and the arrangement position of the adjusting members). For example, a configuration using a ratchet mechanism, etc., may be employed in other configurations.

Function of the First Adjusting Member

Figure 3A:
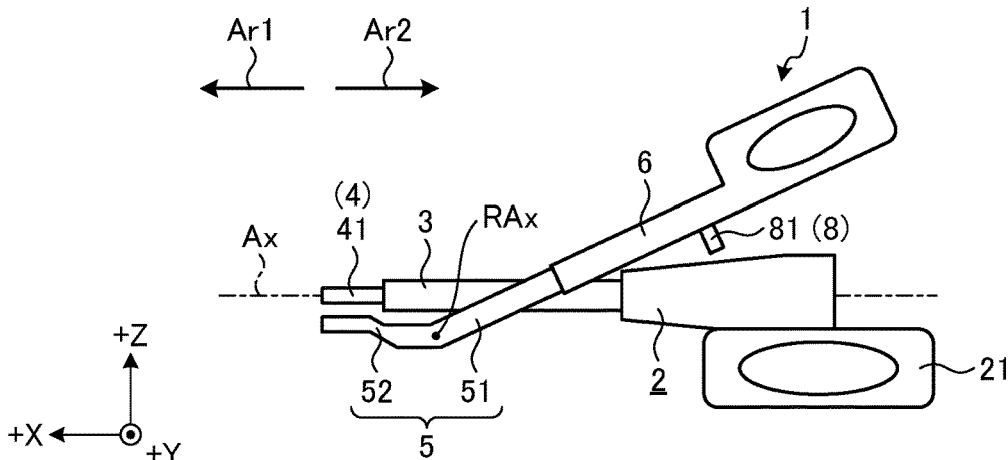
FIG. 3A is a diagram illustrating the function of the first adjusting member.
Figure 3B:
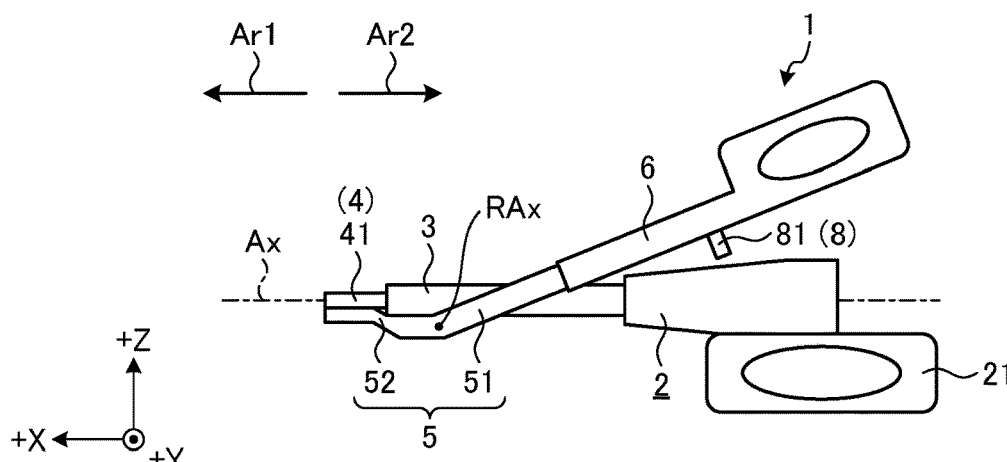
FIG. 3B is a diagram illustrating the function of the first adjusting member.
Figure 3C:
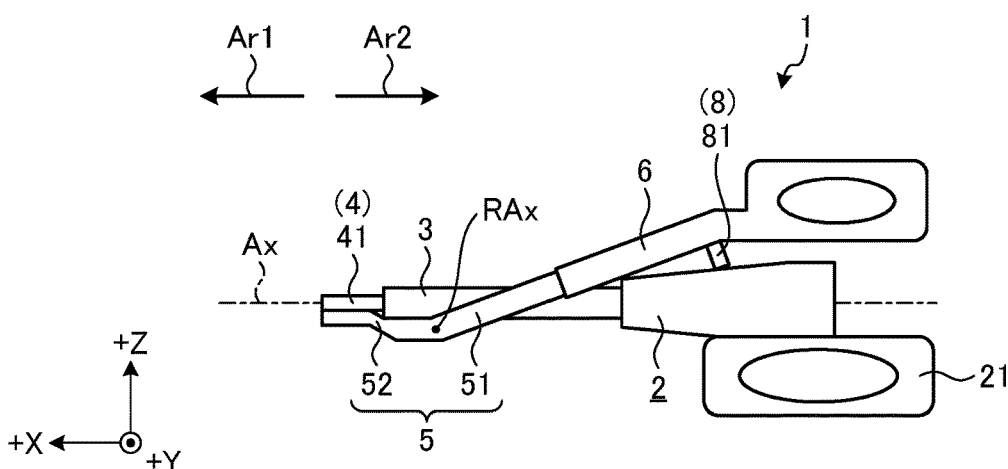
FIG. 3C is a diagram illustrating the function of the first adjusting member.

Next, a function of the first adjusting member 8 will be described. FIG. 3A to FIG. 3C is a diagram illustrating the function of the first adjusting member 8. Specifically, FIGS. 3A to 3C sequentially illustrate the movable handle 6 moving with respect to the fixed handle 2. Incidentally, in FIGS. 3A to 3C, for convenience of explanation, illustration of the ultrasonic transducer 7 and the switch 22 are omitted.

In an initial opened state, the grip portion 52 is separated from the treatment portion 41 (FIG. 3A). Then, from the initial opened state, the movable handle 6 is moved closer to the fixed handle 2 in response to an operator's opening and closing controls on the movable handle 6, and the grip portion 52 comes into contact with the treatment portion 41, as shown in FIG. 3B. Then, in response to an operator's further opening and closing controls on the movable handle 6, the movable handle 6 is further brought into close proximity with respect to the fixed handle 2 until the protruding portion 81 abuts on the fixed handle 2 (FIG. 3C).

In this state (FIG. 3C), a force corresponding to the urging force due to the elastic deformation of the jaw 5 and the movable handle 6 is applied between the treatment portion 41 and the grip portion 52. In other words, the amount of gripping force for grasping the target site between the treatment portion 41 and the grip portion 52 varies depending on the amount or distance of the stroke, i.e., the stroke length, of the movable handle 6 from a state shown in FIG. 3B to a state shown in FIG. 3C, in which the protruding portion 81 abuts the fixed handle 2. More specifically, the larger the stroke length, the larger the biasing force due to the elastic deformation of the jaw 5 and the movable handle 6 is increased and, as a result, the amount of gripping force is also increased. That is, the first adjusting member 8, by changing the amount D0 of the protruding portion 81, changes the value of the stroke length of the movable handle 6 and, as a result, it has a function of adjusting the amount of gripping force.

Method for Producing Procedure Devices

Next, a method of manufacturing the above-described treatment tool 1 will be described. In the following, for convenience of explanation, a method of adjusting the amount of the gripping force will be mainly described. When manufacturing the treatment tool 1, after the treatment tool 1 is assembled, the amount of the gripping force is adjusted as shown below.

Specifically, the operator fixes the treatment tool 1 (fixed handle 2) with respect to an instrument for measurement (such as a force gauge), and sets the condition shown in FIG. 3A. Next, the operator grasps the fixed handle 2 and the movable handle 6 and measures the amount of gripping force between the treatment portion 41 and the grip portion 52 when the condition is set as shown in FIG. 3C (measuring step). For example, a method of measuring the amount of gripping force uses a force gauge, and the method calculates the amount of the gripping force from an amount of distortion of the treatment portion 41 or the grip portion 52. Next, the operator performs the above-described measurement step iteratively, each time changing the amount D0 of the protruding portion 81 to adjust the amount of gripping force until a specific gripping force amount is achieved (adjustment step). Then, after the adjustment process described above, the operator fixes the protruding portion 81 relative to the recess 61 using a fixing member, such as an adhesive, in order to prevent the protruding portion 81 from moving or disengaging. After fixing the protruding portion 81 relative to the recess 61, the operator removes the treatment tool 1 (fixed handle 2) from the instrument for measurement.

According to the first embodiment described above, the following effects can be achieved. The treatment tool 1 according to the first embodiment includes the above-described first adjusting member 8. Therefore, by changing the amount D0 of the protruding portion 81 using the first adjusting member 8, the stroke of the movable range of the movable handle 6 is adjusted to a specific amount and, as a result, it is possible to adjust the amount of gripping force. Accordingly, according to the treatment tool 1 of the fist embodiment, by adjusting the amount of the gripping force using the first adjusting member 8, it is possible to eliminate the variation in the amount of gripping force due to the individual difference of the treatment tool 1 and to stably grasp the target site. In a particular example, the first adjusting member 8 is constituted by a screw member, such as a set screw, and the amount D0 of the protruding portion 81 can be adjusted to (for example, commensurate with the overall length of the first adjusting member 8 and considering the rigidity of the movable handle and jaws, and the arrangement position of the adjusting members). Therefore, it is possible to finely adjust the amount of gripping force and to effectively eliminate the variation in the amount of gripping force due to the individual difference of the treatment tool 1.

Second Embodiment

Next, a second embodiment will be described. In the following description, the same reference numerals will be used for the same configurations as in the first embodiment described above, and detailed description thereof will be omitted or simplified. In the treatment tool 1 according to the second embodiment, the configuration of the first adjusting member 8 is different from that of the treatment tool 1 described in the first embodiment described above. Hereinafter, for convenience of explanation, the first adjusting member according to the second embodiment will be described as a first adjusting member 8A

Figure 4A:
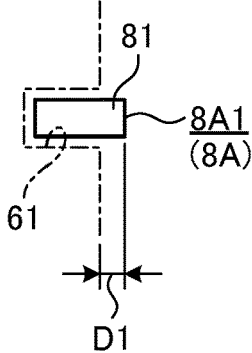
FIG. 4A is a diagram showing a configuration of a first adjusting member according to the second embodiment.
Figure 4B:
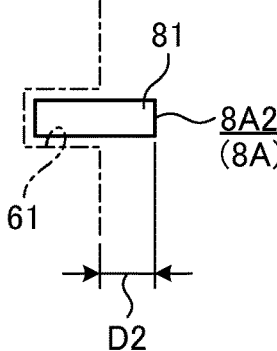
FIG. 4B is a diagram showing a configuration of a first adjusting member according to the second embodiment.
Figure 4C:
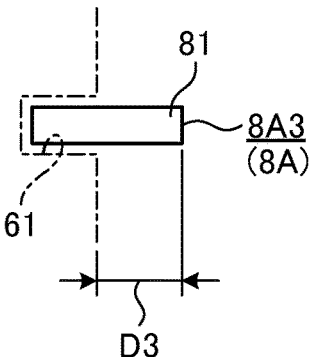
FIG. 4C is a diagram showing a configuration of a first adjusting member according to the second embodiment.

FIG. 4A to FIG. 4C is a diagram showing a configuration of a first adjusting member 8A according to the second embodiment. As shown in FIG. 4A to FIG. 4C, the first adjusting member 8A has three variations, identified as first adjusting member 8A1 to 8A3. As shown in FIGS. 4A to 4C, the three first adjusting member 8A1 to 8A3 each extends linearly and is constituted by a columnar member differing in length from each other. Any of the three first adjusting member 8A1 to 8A3 is then fitted into the recess 61 in the movable handle 6.

Specifically, among the three first adjusting member 8A1 to 8A3, the length of first adjusting member 8A1 is smallest and the length of first adjusting member 8A3 is largest. Then, when each of the three first adjusting member 8A1 to 8A3 is fitted into the recess 61, the protruding portion 81 extends from the recess by a differing protruding amount. For example, when first adjusting member 8A1 (the first adjusting member with the smallest length) is fitted into the recess 61, the protruding portion 81 extends from the recess by the protruding amount D1 (FIG. 4A). Also for example, in a state in which first adjusting member 8A2 is fitted into the recess 61, the protruding portion 81 extends from the recess by the protruding amount D2 (FIG. 4B). Further for example, in a state in which first adjusting member 8A3 is fitted into the recess 61, the protruding portion 81 extends from the recess by the protruding amount D3 (FIG. 4C). The relationship between these protruding amount D1 to D3, i.e., the amounts by which the protruding portions 81 extend from the recess, is $D1<D2<D3$. That is, by changing the length of the first adjusting member 8A to be fitted into the recess 61, the amount by which the protruding portion 81 extends from the recess 61 is changed.

Note that, in the method of manufacturing the treatment tool 1 according to the second embodiment, the only feature that is changed from the method of manufacturing the treatment tool 1 described in the first embodiment is the first adjusting member 8A to be fitted into the recess. Even when the first adjusting member 8A according to the second embodiment described above is employed, the same effect as in the first embodiment described above is achieved.

Third Embodiment

Next, a third embodiment will be described. In the following description, the same reference numerals will be used for the same configurations as in the first embodiment described above, and detailed description thereof will be omitted or simplified. In the treatment tool 1 according to the third embodiment, the configuration of the first adjusting member 8 is different from that of the treatment tool 1 described in the first embodiment described above. Hereinafter, for convenience of explanation, a first adjusting member according to the third embodiment will be described as a first adjusting member 8B.

Figure 5:
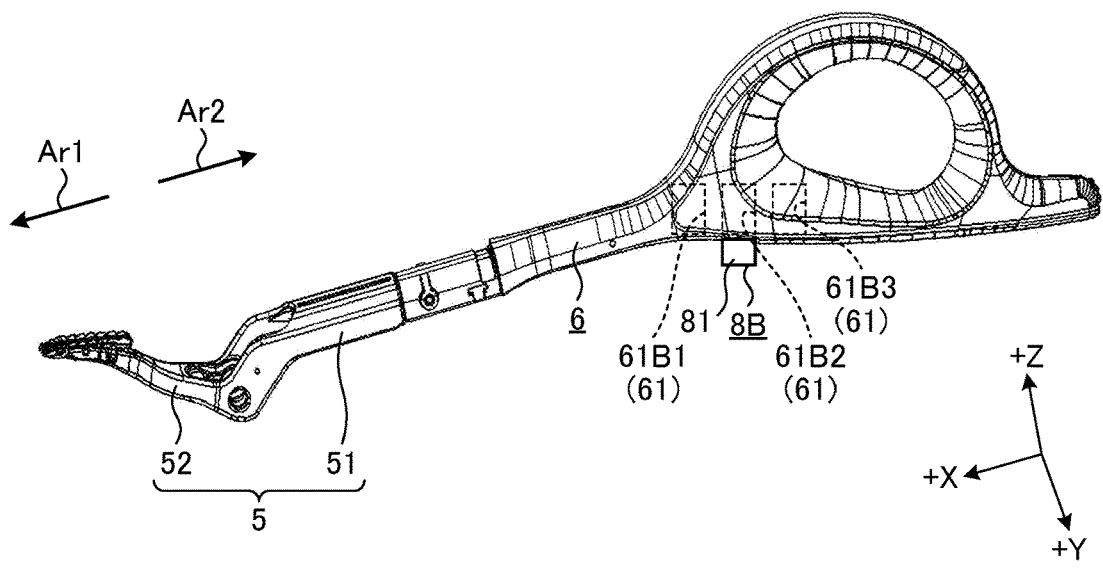
FIG. 5 is a diagram illustrating a configuration of a first adjusting member according to the third embodiment.
Figure 6:
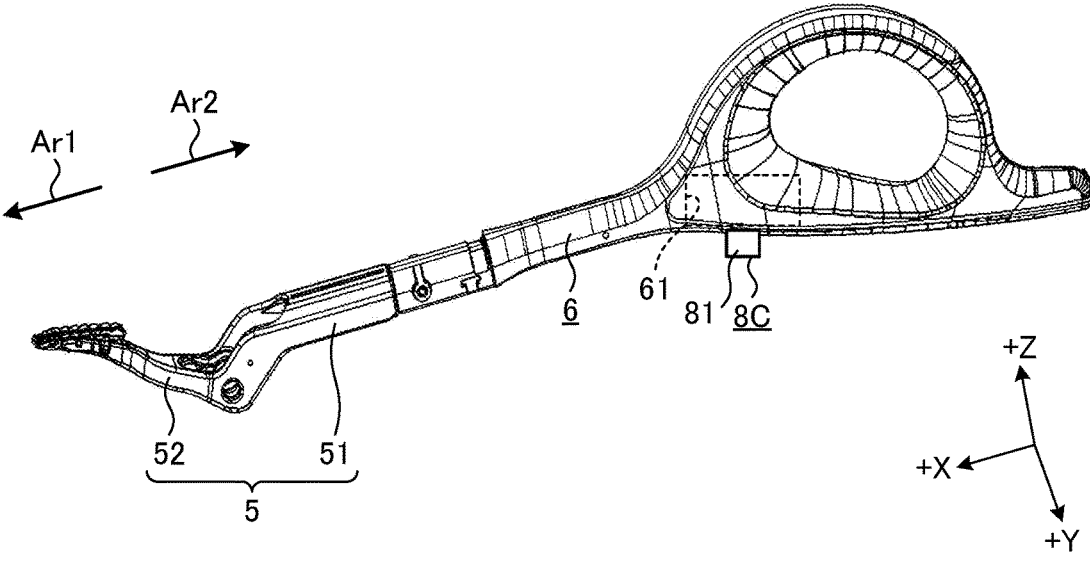
FIG. 6 is a diagram illustrating a configuration of a first adjusting member according to the fourth embodiment.

FIG. 5 is a diagram showing a configuration of a first adjusting member 8B according to the third embodiment. The first adjusting member 8B is constituted by a columnar member extending linearly. As shown in FIG. 5, the recess 61 has three variations, identified as recesses 61B1 to 61B3. The three recesses 61B1 to 61B3 are arranged from the distal end Ar1 toward the proximal end Ar2 along the longitudinal direction of the movable handle 6 in the following order: first recess 61B1, second recess 61B2, and third recess 61B3. The first adjusting member 8B is fitted into any of the first recess 61B1, second recess 61B2, and third recess 61B3. In other words, the first to third recesses 61B1 to 61B3 correspond to the "attachment position with respect to the movable handle" according to the present invention. In the specific third embodiment shown in FIG. 5, the first adjusting member 8B is fitted into the second recess 61B2.

In the third embodiment, even when the first adjusting member 8B is fitted into any of the recesses 61 of the first to third recess 61B1 to 61B3, the projecting amounts of the protruding portions 81 are the same. However, it is also possible to change the depth of the first to third recess 61B1 to 61B3 so as to differ the amount that the protruding portion 81 extends from the recess 61. Hereinafter, for convenience of explanation, a state in which the first adjusting member 8B is fitted into the first recess 61B1 will be described as a first state, a state in which the first adjusting member 8B is fitted into the second recess 61B2 will be described as a second state, and a state in which the first adjusting member 8B is fitted to the third recess 61B3 will be described as a third state. The relationship of the stroke amount that is the movable range of the movable handle 6 in the first to third states is: the stroke amount of the movable handle 6 in the first state is less than the stroke amount of the movable handle 6 in the second state, which is less than the stroke amount of the movable handle 6 in the third state [(stroke amount of the movable handle 6 in the first state)<(the stroke amount of the movable handle 6 in the second state)<(the stroke amount of the movable handle 6 in the third state)].

That is, changing the mounting position of the first adjusting member 8B along the longitudinal direction of the movable handle 6, e.g., by using a different recess among the first to third recess 61B1 to 61B3, changes the stroke amount of the movable range of the movable handle 6 and, as a result, the amount of gripping force is adjusted.

Note that, in the treatment tool 1 according to the third embodiment, the only feature that is changed with respect to the treatment tool 1 described in the first embodiment described above is the attachment position of the first adjusting member 8B with respect to the movable handle 6. Note also that, in the method of manufacturing the treatment tool 1 according to the third embodiment, the only feature that is changed with respect to the method of manufacturing the treatment tool 1 described in the first embodiment described above, is the presence of the first adjusting member 8B in the adjusting process. Even when the first adjusting member 8B according to the third embodiment described above is employed, the same effect as in the first embodiment described above is achieved.

Fourth Embodiment

Next, a fourth embodiment will be described. In the following description, the same reference numerals will be used for the same configurations as in the first embodiment described above, and detailed description thereof will be omitted or simplified. In the treatment tool 1 according to the fourth embodiment, the configuration of the first adjusting member 8 is different from that of the treatment tool 1 described in the first embodiment described above. Hereinafter, for convenience of explanation, the first adjusting member according to the fourth embodiment will be described as a first adjusting member 8C.

Figure 7A:
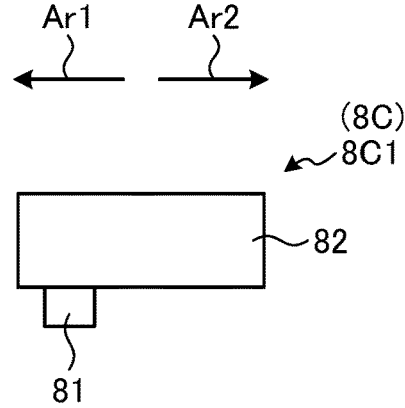
FIG. 7A is a diagram illustrating a configuration of a first adjusting member according to the fourth embodiment.
Figure 7B:
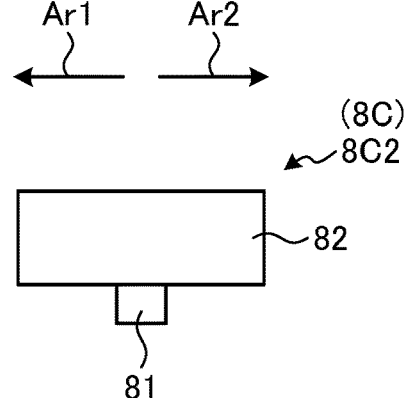
FIG. 7B is a diagram illustrating a configuration of a first adjusting member according to the fourth embodiment.
Figure 7C:
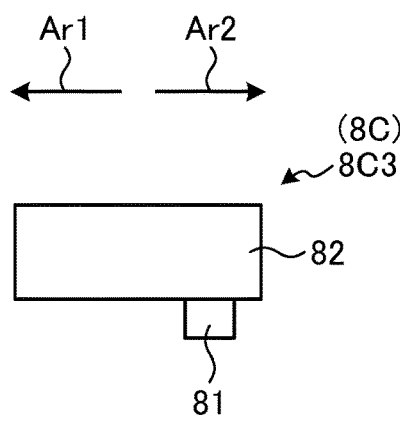
FIG. 7C is a diagram illustrating a configuration of a first adjusting member according to the fourth embodiment.

FIG. 6 and FIGS. 7A to 7C are diagrams showing a configuration of a first adjusting member 8C according to the fourth embodiment. As shown in FIG. 7A to FIG. 7C, the first adjusting member 8C has three variations, identified as first adjusting member 8C1 to 8C3. In each of the three first adjusting members 8C1 to 8C3, a substantially rectangular parallelepiped-shaped fitting portion 82 extending along the lateral direction and a protruding portion 81 is provided on one surface of the fitting portion 82. However, in the three first adjusting members 8C1 to 8C3, the arrangement position of the protruding portion 81 differs from each other. Specifically, in first adjusting member 8C1, the protruding portion 81 is provided at a first end portion of the side surface of the fitting portion 82 in the longitudinal direction of the fitting portion 82 (on the left side as shown in FIG. 7A). In first adjusting member 8C2, the protruding portion 81 is provided at a substantially central position of the side surface of the fitting portion 82 in the longitudinal direction of the fitting portion 82 (in the center as shown in of FIG. 7B). In first adjusting member 8C3, the protruding portion 81 is provided at a second end portion of the side surface of the fitting portion 82 in the longitudinal direction of the fitting portion 82 (on the right side as shown in FIG. 7C). In each of the three first adjusting members 8C1 to 8C3, the fitting portion 82 is then fitted into the recess 61 in a position along the longitudinal direction of the movable handle 6. In the specific fourth embodiment shown in FIG. 6, first adjusting member 8C2 is fitted into the recess 61.

In the fourth embodiment, even when a fitting portion 82 with any of three first adjusting member 8C1 to 8C3 is fitted into the recess 61, the amount by which the protruding portion 81 extends from the recess 61 is the same. It is also possible to provide the protruding portion 81 in the three first adjusting member 8C1 to 8C3 so as to differ the length of the protruding portion 81, and thereby change the amount by which the protruding portion 81 extends from the recess 61.

Hereinafter, for convenience of explanation, a state in which first adjusting member 8C1 is fitted into the recess 61 will be described as a first state, a state in which first adjusting member 8C2 is fitted into the recess 61 is described as a second state, and a state in which first adjusting member 8C3 is fitted into the recess 61 is described as a third state.

The relationship of the stroke amount that is the movable range of the movable handle 6 in the first to third states is: the stroke amount of the movable handle 6 in the first state is less than the stroke amount of the movable handle 6 in the second state which is less than the stroke amount of the movable handle 6 in the third state [(stroke amount of the movable handle 6 in the first state)<(the stroke amount of the movable handle 6 in the second state)<(the stroke amount of the movable handle 6 in the third state)]. That is, changing the first adjusting member 8B along the longitudinal direction of the movable handle 6, e.g., by using a different recess among the first to third recess 61B1 to 61B3, changes the stroke amount of the movable range of the movable handle 6 and, as a result, the amount of gripping force is adjusted.

Note that, in the treatment tool 1 according to the fourth embodiment, the only feature that is changed with respect to the treatment tool 1 described in the first embodiment described above is the first adjusting member 8C to be fitted into the recess 61, with any attendant change in attachment position of the protruding portion 81 with respect to the movable handle 6. Note also that, in the method of manufacturing the treatment tool 1 according to the fourth embodiment, the only feature that is changed with respect to the method of manufacturing the treatment tool 1 described in the first embodiment described above is the presence in the adjusting process of the first adjusting member 8C with any attendant change in attachment position of the protruding portion 81 with respect to the movable handle 6. Even when the first adjusting member 8C according to the fourth embodiment described above is employed, the same effect as in the first embodiment described above is achieved.

Fifth Embodiment

Next, a fifth embodiment will be described. In the following description, the same reference numerals will be used for the same configurations as in the first embodiment described above, and detailed description thereof will be omitted or simplified. In the treatment tool 1 according to the fifth embodiment, a second adjusting member 9 is employed as a configuration for adjusting the gripping force amount with respect to the treatment tool 1 instead of the first adjusting member 8 described in the first embodiment described above.

Figure 8:
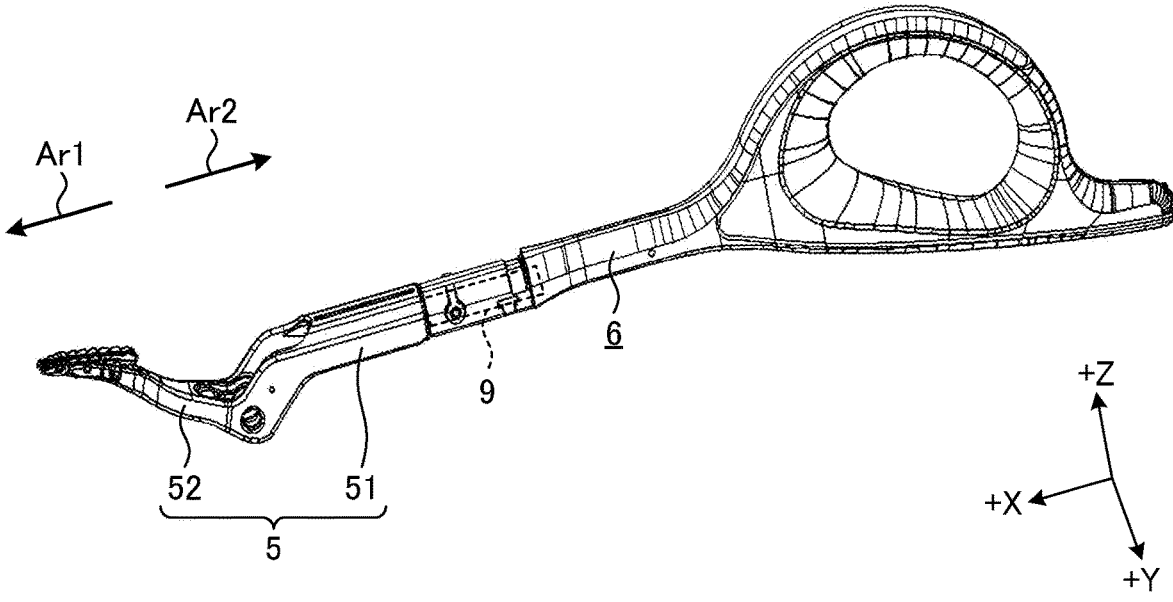
FIG. 8 is a diagram illustrating a configuration of a second adjusting member according to the fifth embodiment.
Figure 9:
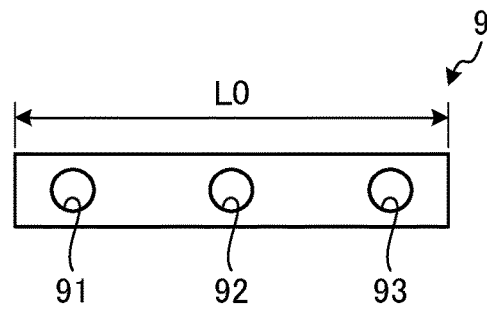
FIG. 9 is a diagram illustrating a configuration of a second adjusting member according to the fifth embodiment.
Figure 10A:
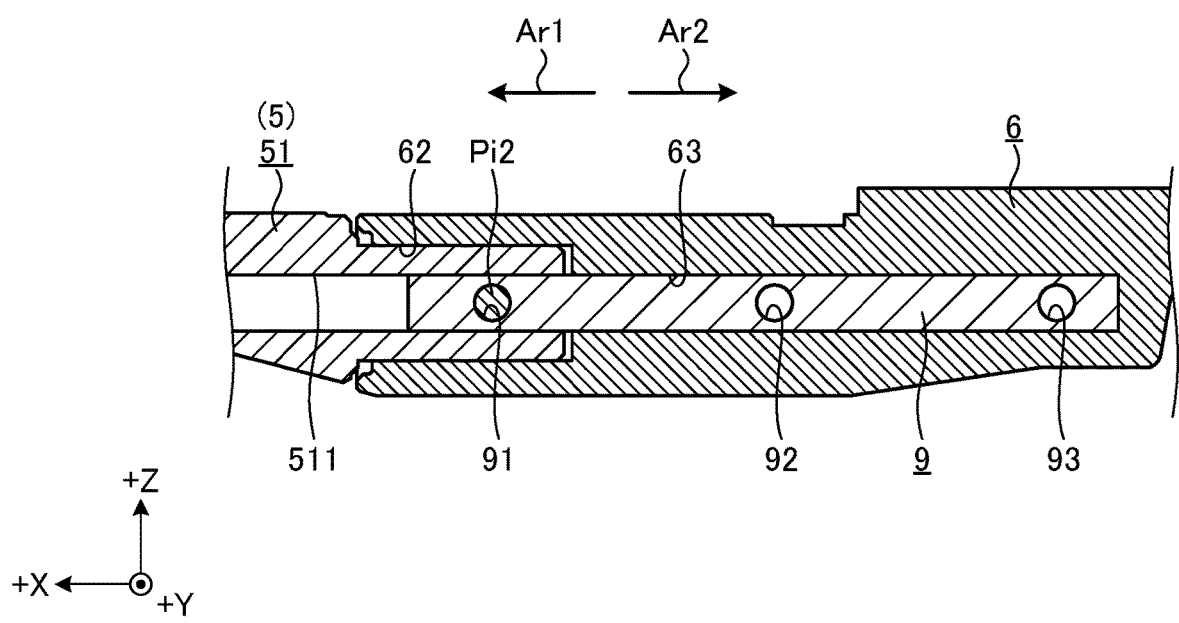
FIG. 10A is a diagram illustrating a configuration of a second adjusting member according to the fifth embodiment.
Figure 10B:
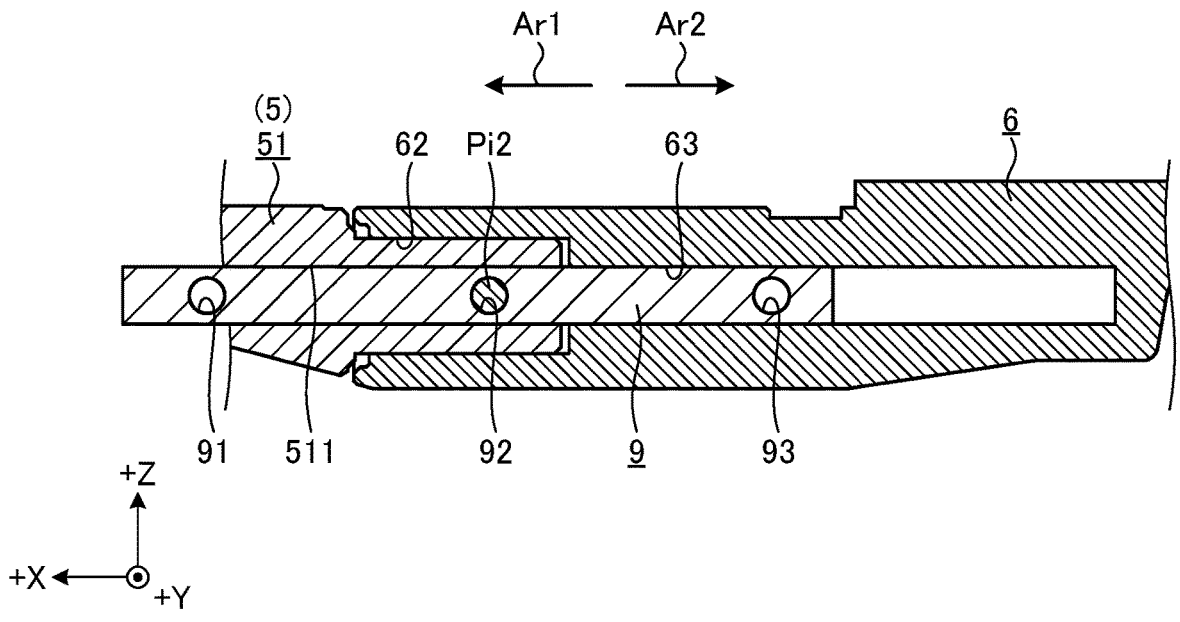
FIG. 10B is a diagram illustrating a configuration of a second adjusting member according to the fifth embodiment.
Figure 10C:
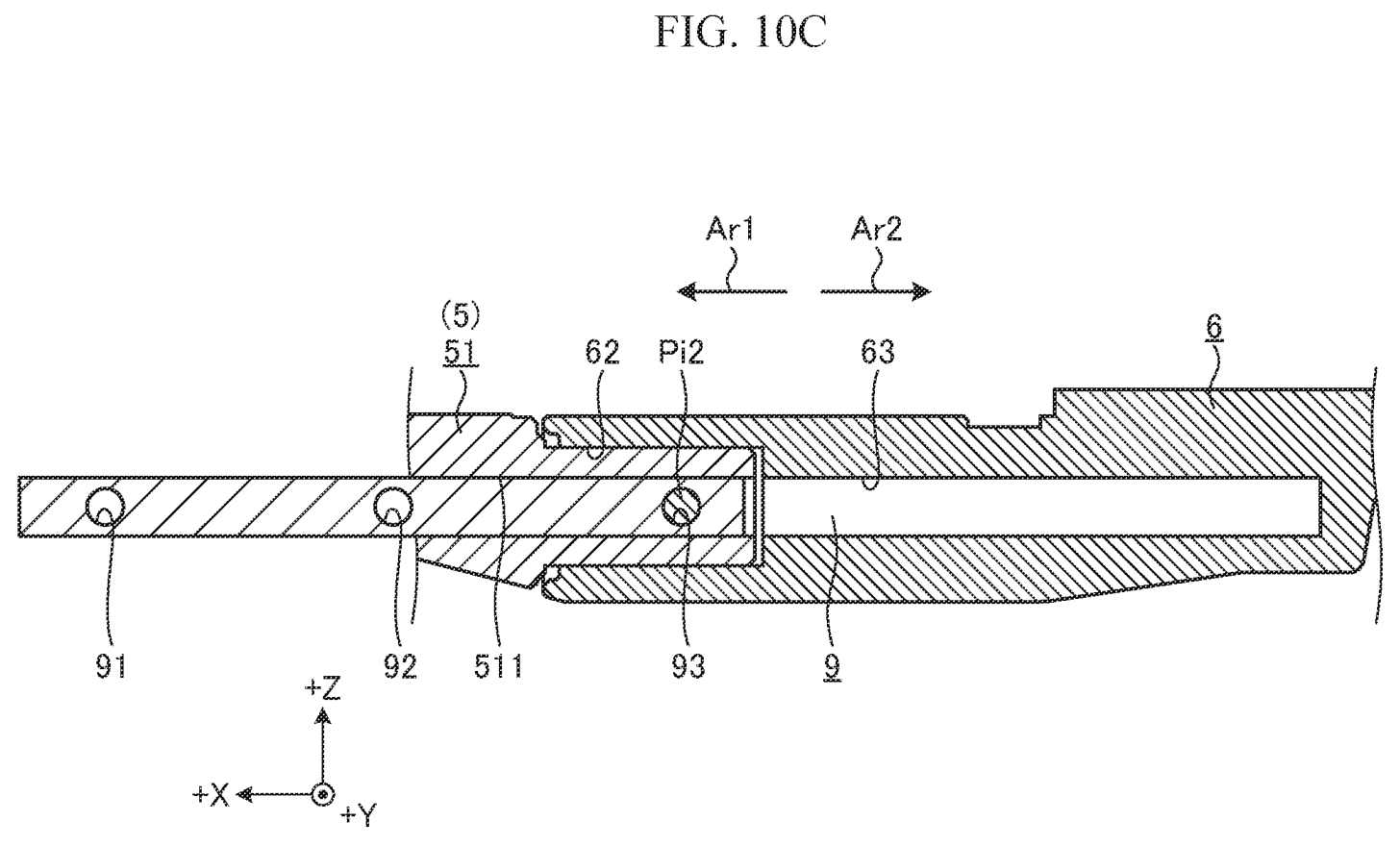

FIG. 8, FIG. 9, and FIGS. 10A to 10C are diagrams showing a configuration of a second adjusting member 9 according to the fifth embodiment. Specifically, FIG. 8 is a perspective view of the jaw 5 and the movable handle 6 and showing second adjusting member 9 arranged internally, FIG. 9 is a diagram showing an embodiment of a second adjusting member 9, and FIGS. 10A to 10C are cross-sectional views of a connecting portion between the jaw 5 and the movable handle 6 cut by the XZ plane and showing different arrangements of the second adjusting member 9.

According to the fifth embodiment and as shown in FIGS. 10A to 10C, the proximal end side Ar2 of the connecting portion 51 extends toward and is connected to the distal end side Ar1 of the movable handle 6, and the end face of the proximal end side Ar2 of the connecting portion 51 includes a first insertion hole 511 to allow insertion of a first portion of the second adjusting member 9 and the end face of the distal end side Ar1 of the movable handle 6 includes a second insertion hole 63 to allow insertion of a second portion of the second adjusting member 9. Furthermore and as shown in FIGS. 10A to 10C, in the fifth embodiment, the end face of the distal end side Ar1 of the movable handle 6 includes a connecting recess 62 that extends toward the proximal end side Ar2 and the end portion of the proximal end side Ar2 of the connecting portion 51 is inserted into the connecting recess 62. The connecting portion 51 is connected to the movable handle 6 by inserting one or more fasteners. For example, pin Pi2 (see FIGS. 10A to 10C) is inserted through the end portion of the proximal end side Ar2 of the connecting portion 51 and the end portion of the distal end side Ar1 of the movable handle 6 while the end portion of the proximal Ar2 is inserted into the connecting recess 62.

Furthermore and as shown in FIGS. 10A to 10C, the movable handle 6 includes a second insertion hole 63 that extends toward the base end side Ar2 from the bottom surface of the connecting recess 62. The second insertion hole 63 is provided to allow insertion of the second adjusting member 9.

The second adjusting member 9 is made from a material having a rigidity, such as metal, and is constituted by an elongated flat plate having a length dimension L0 (see FIG. 9). Herein, rigidity is measured using Young's modulus. As shown in FIGS. 8, 9, and 10A to 10C, the second adjusting member 9 is provided inside the connecting portion 51 and the movable handle 6 to increase the stiffness of the jaws 5 and/or the movable handle 6.

As shown in FIGS. 9 and 10A to 10C, the second adjusting member 9 is provided with three through holes 91 to 93 penetrating the respective plate surfaces. Here, the first through hole 91 is provided in the second adjusting member 9 at a first end of the second adjusting member 9 in the longitudinal direction (on the left side as shown in FIGS. 9 and 10A to 10C), the second through hole 92 is provided in a substantially central position in the longitudinal direction of the second adjusting member 9 (in the center as shown in FIGS. 9 and 10A to 10C), and the third through hole 93 is provided in the second adjusting member 9 at a second end of the second adjusting member 9 in the longitudinal direction (on the right side as shown in FIGS. 9 and 10A to 10C).

The second adjusting member 9 can be mounted to the jaw 5 and the movable handle 6 in the respective states of the first to third states described below.

The first state is shown in FIG. 10A. In the first state, a first portion of the second adjusting member 9 with the first through hole 91, i.e., the portion located on the left side (one end side in the longitudinal direction), is inserted into the first insertion hole 511 and a second portion of the second adjusting member 9, i.e., the portion located on the right side (the other end side in the longitudinal direction) is inserted into the second insertion hole 63. Then, the second adjusting member 9 is attached to the jaw 5 and to the movable handle 6 with the pin Pi2 penetrating the first through hole 91.

The second state is shown in FIG. 10B. In the second state, a first portion of the second adjusting member 9 with the first through hole 91 and the second through hole 92, i.e., the portion located on the left side (one end side in the longitudinal direction), is inserted into the first insertion hole 511 and a second portion of the second adjusting member 9, i.e., the portion located on the right side (the other end side in the longitudinal direction) is inserted into the second insertion hole 63. Then, the second adjusting member 9 is attached to the jaw 5 and to the movable handle 6 with the pin Pi2 penetrating the second through hole 92.

The third state is shown in FIG. 10C. In the third state, a first portion of the second adjusting member 9 with the first through hole 91, the second through hole 92, and the third through hole 93, i.e., the portion located on the left side (one end side in the longitudinal direction), is inserted into the first insertion hole 511. In some embodiments of the third state, and the entire second adjusting member 9 is inserted into the first insertion hole 511 and in other embodiments of the third state, a second portion of the second adjusting member 9, i.e., the portion located on the right side (the other end side in the longitudinal direction) is inserted into the second insertion hole 63. Then, the second adjusting member 9 is attached to the jaw 5 and to the movable handle 6 with the pin Pi2 penetrating the third through hole 93.

Here, the jaw 5 is composed of a metal material and the movable handle 6 is made of a resin material. Therefore, the longer (in the longitudinal direction) the portion of the second adjusting member 9, which is composed of a metal material, is inserted into the movable handle 6, the more the rigidity of the jaw 5 and the movable handle 6 is increased. In other words, among the first to third states described above, the stiffness of the jaw 5 and the movable handle 6 is highest in the first state and lowest in the third state.

Also, in the case where the treatment portion 41 and the grip portion 52 are in contact with each other (see state shown in FIG. 3B) and the movable handle 6 is then brought close to the fixed handle 2 in response to the opening and closing control to the movable handle 6 (see state shown in FIG. 3C), the force (amount of gripping force) applied between the treatment portion 41 and the grip portion 52 according to the biasing force due to the elastic deformation of the jaw 5 and the movable handle 6 is larger when the rigidity of the jaw 5 and the movable handle 6 is higher. In other words, the second adjusting member 9 has a function of changing the stiffness of the jaw 5 and the movable handle 6 by adjusting the mounting position with respect to the jaw 5 and the movable handle 6, and as a result, adjusting the amount of the gripping force.

Note that, in the treatment tool 1 according to the fifth embodiment, the only feature that is changed with respect to the treatment tool 1 described in the first embodiment described above is the second adjusting member 9 instead of the first adjusting member 8. Note also that, in the method of manufacturing the treatment tool 1 according to the fifth embodiment, the only feature that is changed with respect to the method of manufacturing the treatment tool 1 described in the first embodiment described above is the presence in the adjusting process of the second adjusting member 9 with the attendant changing of the attachment position of the second adjusting member 9 with respect to the jaw 5 and the movable handle 6. Here, the pin Pi2 functions as a fixing member for fixing the second adjusting member 9 with respect to the movable handle 6.

According to the fifth embodiment described above, the following effects can be obtained. The treatment tool 1 according to the fifth embodiment includes the second adjusting member 9 described above. Therefore, by changing the rigidity of the jaw 5 and the movable handle 6 using the second adjusting member 9, it is possible to adjust the amount of gripping force. Therefore, even when the second adjusting member 9 according to the fifth embodiment is employed, the same effect as in the first embodiment described above is achieved.

Sixth Embodiment

Next, a sixth embodiment will be described. In the following description, the same reference numerals will be used for the same configurations as in the fifth embodiment described above, and detailed description thereof will be omitted or simplified. In the treatment tool 1 according to the sixth embodiment, the configuration of the second adjusting member 9 is different from that of the treatment tool 1 described in the fifth embodiment described above. Hereinafter, for convenience of explanation, a second adjusting member according to the sixth embodiment will be described as a second adjusting member 9A.

Figure 11A:
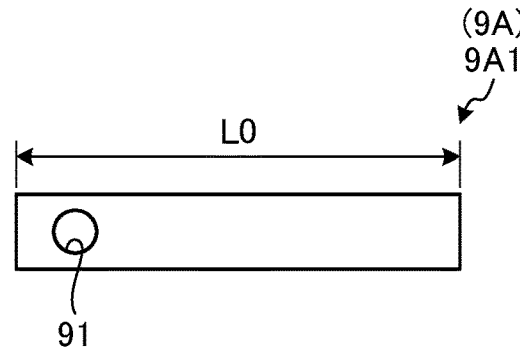
FIG. 11A is a diagram showing a configuration of a second adjusting member according to the sixth embodiment.
Figure 11B:
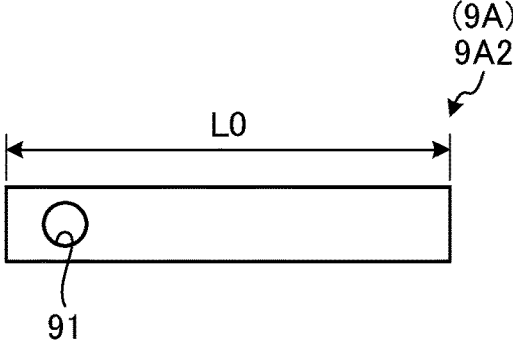
FIG. 11B is a diagram showing a configuration of a second adjusting member according to the sixth embodiment.
Figure 11C:
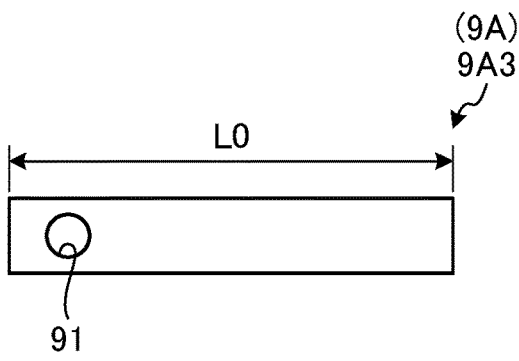
FIG. 11C is a diagram showing a configuration of a second adjusting member according to the sixth embodiment.

FIGS. 11A to 11C show a configuration of a second adjusting member 9A according to the sixth embodiment. As shown in FIGS. 11A to 11C, the second adjusting member 9A has three variations, identified as second adjusting member 9A1 to 9A3. As shown in FIGS. 11A to 11C, each of the three second adjusting members 9A1 to 9A3 has the same outer shape as the second adjusting member 9 described in the fifth embodiment described above. Any of the three second adjusting member 9A1 to 9A3 is then attached to the jaw 5 and the movable handle 6. Here, only the first through hole 91 (from among the first to third through holes 91 to 93 described in the fifth embodiment described above) is provided in the three second adjusting members 9A1 to 9A3. That is, each of the three second adjusting members 9A1 to 9A3 is attached to the jaw 5 and the movable handle 6, respectively, only in a way corresponding to the first state described in the fifth embodiment described above (see FIG. 10A).

The three second adjusting members 9A1 to 9A3 differ in stiffness from each other by differing in material properties from each other. Specifically, among the three second adjusting members 9A1 to 9A3, the rigidity of the second adjusting member 9A1 is lowest, the rigidity of the second adjusting member 9A3 is highest. That is, among the three second adjusting members 9A1 to 9A3, when second adjusting member 9A1 is attached to the jaw 5 and the movable handle 6, the stiffness of the jaw 5 and the movable handle 6 is lowest, and as a result, the amount of gripping force is smallest. Example amounts of gripping force in the case when second adjusting member 9A1 is attached to the jaw 5 and the movable handle 6 is 100 to 220 KN/m². Further, among the three second adjusting members 9A1 to 9A3, when second adjusting member 9A3 is attached to the jaw 5 and the movable handle 6, the stiffness of the jaw 5 and the movable handle 6 is highest, and as a result, the amount of the gripping force quantity is greatest. Example amounts of gripping force in the case when second adjusting member 9A3 is attached to the jaw 5 and the movable handle 6 is 100 to 220 KN/m².

Note that, in the treatment tool 1 according to the sixth embodiment, the only feature that is changed with respect to the treatment tool 1 described in the fifth embodiment described above is the second adjusting member 9A instead of the second adjusting member 9. Note also that, in the method of manufacturing the treatment tool 1 according to the fifth embodiment, the only feature that is changed with respect to the method of manufacturing the treatment tool 1 described in the fifth embodiment described above is the presence in the adjusting process of the second adjusting member 9A with the attendant changing of the rigidity of the second adjusting member 9A. Even when the second adjusting member 9A according to the sixth embodiment described above is employed, the same effect as in the fifth embodiment described above is achieved.

Seventh Embodiment

Next, a seventh embodiment will be described. In the following description, the same reference numerals will be used for the same configurations as in fifth embodiment described above, and detailed description thereof will be omitted or simplified. In the treatment tool 1 according to the seventh embodiment, the configuration of the second adjusting member 9 is different from that of the treatment tool 1 described in the fifth embodiment described above. Hereinafter, for convenience of explanation, a second adjusting member according to the seventh embodiment will be described as a second adjusting member 9B.

Figure 12A:
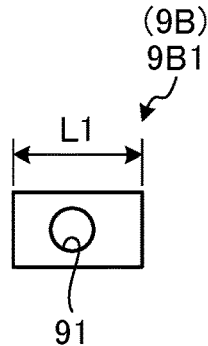
FIG. 12A is a diagram showing a configuration of a second adjusting member according to the seventh embodiment.
Figure 12B:
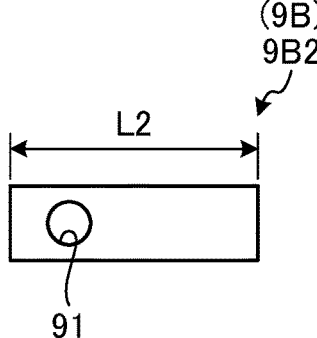
FIG. 12B is a diagram showing a configuration of a second adjusting member according to the seventh embodiment.
Figure 12C:
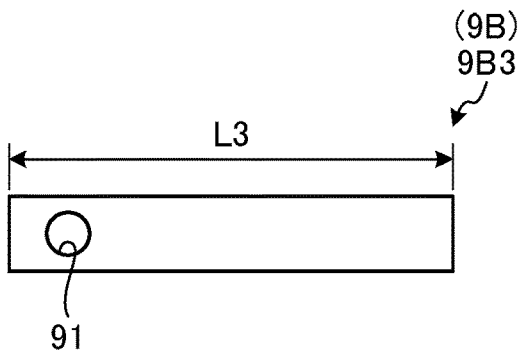
FIG. 12C is a diagram showing a configuration of a second adjusting member according to the seventh embodiment.

FIGS. 12A to 12C show a configuration of a second adjusting member 9B according to the seventh embodiment. As shown in FIGS. 12A to 12C, the second adjusting member 9B has three variations, identified as second adjusting member 9B1 to 9B3. As shown in FIGS. 12A to 12C, the three second adjusting member 9B1 have an outer shape that is changed only in the length dimension and number of through holes with respect to the second adjusting member 9 described in the fifth embodiment described above. Any of the three second adjusting members 9B1 to 9B3 is attached to the jaw 5 and the movable handle 6. Here, only the first through hole 91 (from among the first to third through holes 91 to 93 described in the fifth embodiment described above) is provided in the three second adjusting member 9B1 to 9B3. That is, each of the three second adjusting member 9B1 to 9B3 is attached to the jaw 5 and the movable handle 6, respectively, only in a way corresponding to the first state described in the fifth embodiment described above (see FIG. 10A).

Specifically, the relation between the length dimensions L1 to L3 of the three second adjusting member 9B1 to 9B3 is L1<L2<L3. In other words, among the three second adjusting members 9B1 to 9B3, when second adjusting member 9B1 is attached to the jaw 5 and the movable handle 6, the portion where the second adjusting member 9B1 enters into the inside of the movable handle 6 is smallest, and the stiffness of the jaw 5 and the movable handle 6 is lowest. Therefore, the amount of gripping force is the smallest. In addition, among the three second adjusting member 9B1 to 9B3, when second adjusting member 9B3 is attached to the jaw 5 and the movable handle 6, the portion where the second adjusting member 9B3 enters into the inside of the movable handle 6 becomes largest, and the stiffness of the jaw 5 and the movable handle 6 is highest. Therefore, the amount of gripping force is greatest.

Note that, in the treatment tool 1 according to the seventh embodiment, the only feature that is changed with respect to the treatment tool 1 described in the fifth embodiment described above is the second adjusting member 9B instead of the second adjusting member 9. Note also that, in the method of manufacturing the treatment tool 1 according to the seventh embodiment, the only feature that is changed with respect to the method of manufacturing the treatment tool 1 described in the fifth embodiment described above is the presence in the adjusting process of the second adjusting member 9B. Even when the second adjusting member 9B according to the seventh embodiment described above is employed, the same effect as in the fifth embodiment described above is achieved.

Eighth Embodiment

Next, an eighth embodiment will be described. In the following description, the same reference numerals will be used for the same configurations as in the fifth embodiment described above, and detailed description thereof will be omitted or simplified. In the treatment tool 1 according to the eighth embodiment, the configuration of the second adjusting member 9 is different from that of the treatment tool 1 described in the fifth embodiment described above. Hereinafter, for convenience of explanation, a second adjusting member according to the eighth embodiment will be described as a second adjusting member 9C.

Figure 13:
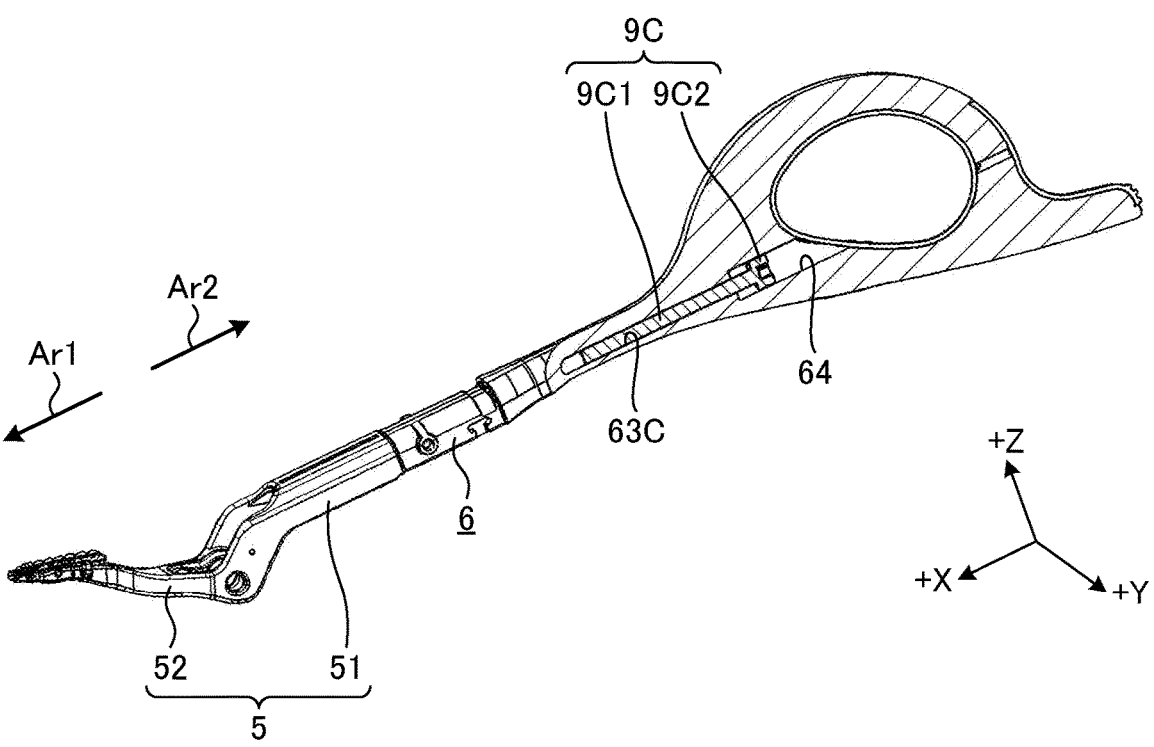
FIG. 13 is a diagram illustrating a configuration of a second adjusting member according to the eighth embodiment.

FIG. 13 is a diagram illustrating a configuration of a second adjusting member 9C according to the eighth embodiment. In FIG. 13, a portion of the movable handle 6 is cut by the XZ plane. As shown in FIG. 13, the second adjusting member 9C includes a screw portion 9C1 having threads on the outer peripheral surface, and a screw head 9C2 provided at one end of the screw portion 9C1.

As shown in FIG. 13, the movable handle 6 according to the eighth embodiment includes a third insertion hole 64 communicating with the outside and extending into the interior of the movable handle 6 toward the distal end-side Ar1 along the longitudinal direction of the movable handle 6 to communicate with the second insertion hole 63C. Further, according to the eighth embodiment, the inner peripheral surface of the second insertion hole 63C includes a grooved portion that corresponds to the threaded portion 9C1 of the second adjusting member 9C. Hereinafter, for convenience of explanation, a second insertion hole according to the eighth embodiment will be described as a second insertion hole 63C.

The second adjusting member 9C is attached to the movable handle 6 For example, the second adjusting member 9C is inserted into the second insertion hole 63C from the insertion hole 64, by screwing the screw portion 9C1 to the second insertion hole 63C. A tool, such as a screwdriver, can assist with this process and is inserted into the insertion hole 64 and manipulated to operate the screw head 9C2 to change the screwed state of the screw portion 9C1 relative to the second insertion hole 63C. By adjusting the second adjusting member 9C in the interior of the movable handle 6, e.g., by moving the second adjusting member 9C back and forth along the longitudinal direction of the movable handle 6, the position of the second adjusting member 9C in the interior of the movable handle 6 is changed, which changes the stiffness of the jaw 5 and the movable handle 6, so that the amount of gripping force is adjusted.

Note that, in the treatment tool 1 according to the eighth embodiment, the only feature that is changed with respect to the treatment tool 1 described in the fifth embodiment described above is the second adjusting member 9C instead of the second adjusting member 9. Note also that, in the method of manufacturing the treatment tool 1 according to the eighth embodiment, the only feature that is changed with respect to the method of manufacturing the treatment tool 1 described in the first embodiment described above is the presence in the adjusting process of the second adjusting member 9C and changing the position of the second adjusting member 9C inside the movable handle 6. Even when the second adjusting member 9C according to the eighth embodiment described above is employed, the same effect as in the fifth embodiment described above is achieved.

Ninth Embodiment

Next, a ninth embodiment will be described. In the following description, the same reference numerals will be used for the same configurations as in the fifth embodiment described above, and detailed description thereof will be omitted or simplified. In the treatment tool 1 according to the ninth embodiment, the configuration of the second adjusting member 9 is different from that of the treatment tool 1 described in the fifth embodiment described above. Hereinafter, for convenience of explanation, a second adjusting member according to the ninth embodiment will be described as a second adjusting member 9D.

Figure 14:
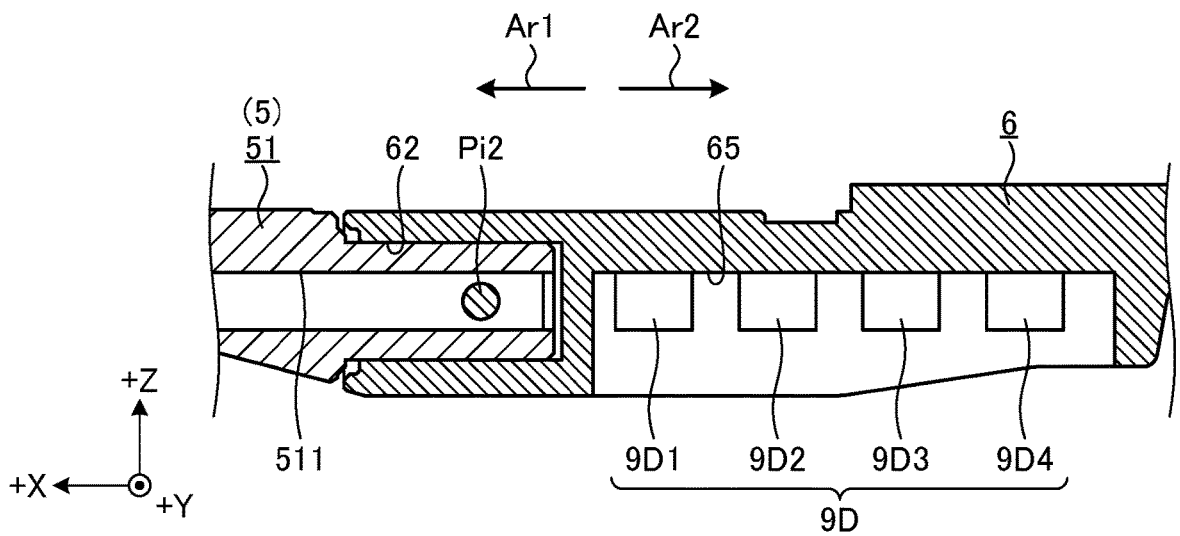
FIG. 14 is a diagram illustrating a configuration of a second adjusting member according to the ninth embodiment.

FIG. 14 illustrates a configuration of a second adjusting member 9D according to the ninth embodiment. Specifically, FIG. 14 is a cross-sectional view corresponding to FIG. 10A.

In the movable handle 6 according to the ninth embodiment, a second insertion hole 63 is omitted with respect to the movable handle 6 described in the fifth embodiment described above. Further, in the movable handle 6 in a region toward the in the proximal end side Ar2 relative to the connecting recess 62, mounting holes 65 are included that are recessed toward the +Z-axis side from the side surface of the −Z-axis side. As shown in FIG. 14, the second adjusting member 9D is provided as a plurality of second adjusting member, such as the four second adjusting members 9D1 to 9D4, but any number of second adjusting members can be used. Each of the four second adjusting members 9D1 to 9D4 is substantially a square-shaped, flat plate (in a plane view). At least one of the four second adjusting members 9D1 to 9D4 is fixed to the interior of the mounting hole 65. As the method of fixing, press fit can be exemplified. Further, the stiffness of the movable handle 6 can be changed by changing the number and position of the second adjusting member 9D that are fixed to the inside of the mounting hole 65 and, as a result, the amount of gripping force is adjusted.

Note that, in the method of manufacturing the treatment tool 1 according to the ninth embodiment, only the point of changing the number and the position of the second adjusting member 9D to be fixed to the inside of the mounting hole 65 in the adjusting process is different from the method of manufacturing the treatment tool 1 described in the fifth embodiment described above. Even when the second adjusting member 9D according to the ninth embodiment described above is employed, the same effect as in the fifth embodiment described above is achieved.

Other Embodiments

While embodiments for carrying out the present invention have been described above, the present invention is not to be limited only by the first to ninth embodiments described above.

In the first to fifth embodiments described above, a configuration in which both ultrasonic energy and high frequency energy are applied to a target site is employed, but the present invention is not limited thereto. For example, a configuration in which only ultrasonic energy is applied to a target site, a configuration in which only high frequency energy is applied to a target site, a configuration in which only other energy other than ultrasonic energy and high frequency energy is applied to a target site, or a configuration in which a combination of energy types are applied to a target may be employed.

In the second embodiment described above, the first adjusting member 8A is not limited to three first adjusting members (8A1 to 8A3), and two or four or more first adjusting members 8A may be provided, as long as the length dimensions are different.

In the third embodiment described above, the recess 61 is not limited to three recesses (61B1 to 61B3), and two or four or more recesses 61 may be provided along the longitudinal direction of the movable handle 6.

In the fourth embodiment described above, the first adjusting member 8C is not limited to three first adjusting members (8C1 to 8C3), and two or four or more first adjusting members 8C may be provided as long as the arrangement positions of the protruding portions 81 are different.

In the fifth embodiment described above, the number of through holes is not limited to three through holes (91 to 93), and two or four or more through holes may be provided along the longitudinal direction of the second adjusting member 9.

In the sixth embodiment described above, the second adjusting member 9A is not limited to three second adjusting members (9A1 to 9A3), and two or four or more second adjusting members 9A may be provided, as long as the material properties are different.

In the seventh embodiment described above, the second adjusting member 9B is not limited to three second adjusting members (9B1 to 9B3), and two or four or more second adjusting members 9B may be provided, as long as the length dimensions are different.

In the ninth embodiment described above, the second adjusting member 9D is not limited to four second adjusting members (9D1 to 9D4), and two or three or five or more second adjusting members 9D may be provided.

In the first to fourth embodiments described above, the first adjusting member 8 is provided on the movable handle 6, but the present invention is not limited thereto, and the first adjusting member 8 may be provided on the fixed handle 2 in a state having the same function as that provided on the movable handle 6.

Figure 15:
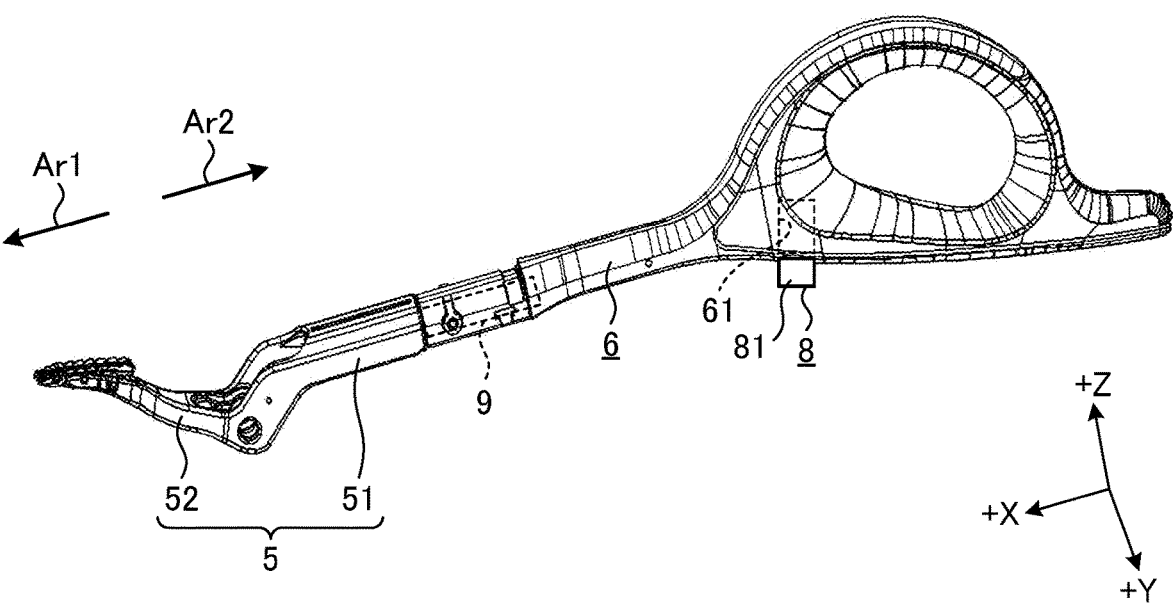
FIG. 15 is a diagram illustrating a modification of the first through ninth embodiments.

FIG. 15 is a diagram illustrating a modification of the first to ninth embodiments. The modification of the treatment tool 1 includes both a first adjusting member 8 and a second adjusting member 9 and the modification of the treatment tool 1 shown in FIG. 15 FIG. 15 shows a case where the second adjusting member 9 described in the above-described fifth embodiment is employed with respect to the treatment tool 1 according to the first embodiment described above. However, the modification of the treatment tool 1 to include both a first adjusting member 8 and a second adjusting member 9 can implement as the first adjusting member 8 any of the first adjusting members described in the first to fourth embodiments described herein and can implement as the second adjusting member 9 any of the second adjusting members described in the fifth to ninth embodiments described herein.

DESCRIPTION OF SYMBOLS

1 Treatment Tool
2 Fixed handle
3 Shaft
4 Vibration transmission member
5 Jaw
6 Movable handle
7 Ultrasonic transducer
8, 8A,8A1-8A3,8B,8C,8C1-8C3 first adjusting member
9, 9A,9A1-9A3,9B,9B1-9B3,9C,9D,9D1-9D4 second adjusting member
9C1 screw
9C2 screw head
21 Handle body
22 Switch
41 Treatment portion.

51 Connecting portion
52 Grip portion
61 Recess
61B1 first recess
61B2 second recess
61B3 third recess
62 Connecting recess
63, 63C second insertion hole
64 Insertion hole
65 Mounting hole
81 Protruding portion
82 Fitting portion
91 First through hole
92 Second through hole
93 Third through hole
511 First insertion hole
Ar1 distal side end
Ar2 proximal side end
Ax central axis
D0-D3 amount of protruding portion, i.e., length
L0-L3 linear dimension
Pi1,Pi2 Pin
RAx rotation shaft

What is claimed is:

1. A treatment tool, comprising:
a fixed handle;
a treatment portion;
a jaw configured to rotate about a rotation axis relative to the treatment portion;
a movable handle configured to operate the jaw; and
a first protrusion disposed at the movable handle,
wherein the movable handle includes a plurality of recesses, the plurality of recesses is arranged along a longitudinal direction of the movable handle, and each of the plurality of recesses is configured to receive the first protrusion,
wherein each recess of the plurality of recesses is separated from an adjacent one of the plurality of recesses by a portion of the movable handle,
wherein the first protrusion extends from a surface of the movable handle toward the fixed handle and the first protrusion is configured to contact the fixed handle when the movable handle is moved toward to the fixed handle, and
wherein an amount of a stroke of the movable handle is adjustable by at least one of (i) adjusting an amount that the first protrusion extends from the surface of the movable handle and (ii) adjusting a location of the first protrusion on the movable handle in the longitudinal direction of the movable handle.

2. The treatment tool according claim 1, further comprising a second protrusion disposed at the movable handle,
wherein the first protrusion extends from the surface of the movable handle toward the fixed handle by the first protruding amount, and
wherein the second protrusion extends from the surface of the movable handle toward the fixed handle by a second protruding amount.

3. The treatment tool according to claim 1, wherein adjusting the location of the first protrusion includes changing in which of the plurality of recesses the first protrusion is disposed.

4. The treatment tool according claim 1, further comprising a second protrusion disposed at the movable handle,
wherein the first protrusion extends from the surface of the movable handle toward the fixed handle by the first protruding amount, wherein the second protrusion extends from the surface of the movable handle toward the fixed handle by a second protruding amount, wherein the first protruding amount is different from the second protruding amount, and wherein one of the first protrusion and the second protrusion is disposed in one of the plurality of recesses.

5. The treatment tool according claim 1, wherein the first protrusion includes a fitting portion and the first protrusion is provided on one surface of the fitting portion, and wherein the movable handle includes a recess configured to receive the fitting portion of the first protrusion.

6. The treatment tool according claim 1, wherein the treatment portion is configured to treat a living tissue positioned between the jaw and the treatment portion by ultrasonic vibration.

7. A manufacturing method of the treatment tool according to claim 1, comprising:

measuring an amount of a gripping force between the treatment portion and the jaw when the fixed handle and the movable handle are gripped; and adjusting the amount of the gripping force to a specific amount by adjusting the amount of the stroke of the movable handle.

8. The treatment tool according claim 1, further comprising:

a shaft extended from the fixed handle in the longitudinal direction, wherein the treatment portion projects distally from a distal end of the shaft, the treatment portion is configured to treat a living tissue, wherein the jaw is configured to rotate to hold the living tissue between the jaw and the treatment portion, and wherein the movable handle is extended from the jaw in a proximal direction, the movable handle configured to move relative to the fixed handle between a furthest position and a closest position defining the stroke of the movable handle and so as to move the jaw to open or close against the treatment portion.

9. The treatment tool according claim 1, wherein when the first protrusion contacts the fixed handle and the movable handle receives a gripping force, the movable handle is configured to be deformed by the gripping force.

10. A treatment tool, comprising:

a fixed handle;

a treatment portion;

a jaw configured to rotate about a rotation axis relative to the treatment portion;

a movable handle configured to operate the jaw; and a second adjusting member disposed inside one or more of the movable handle and the jaw, the second adjusting member configured to adjust a rigidity of the one or more of the movable handle and the jaw, wherein the second adjusting member includes a thread part threadedly connected to the inside of the one or more of the movable handle and the jaw.

11. The treatment tool according claim 10, wherein the second adjusting member is an elongated plate having a length dimension L0, wherein the one or more of the movable handle and the jaw inside which the second adjusting member disposed is made of a first material having a first Young's modulus and the second adjusting member is made from a second material having a second Young's modulus, and wherein the second Young's modulus is greater than the first Young's modulus.

12. The treatment tool according claim 10, wherein the second adjusting member is configured to change an attachment position inside the one or more of the movable handle and the jaw in a longitudinal direction of the one or more of the movable handle and the jaw so as to adjust the rigidity of the one or more of the movable handle and the jaw.

13. The treatment tool according claim 10, further comprising a third adjusting member disposed inside the one or more of the movable handle and the jaw, the third adjusting member configured to adjust the rigidity of the one or more of the movable handle and the jaw, wherein the second adjusting member has a different shape from the third adjusting member.

14. The treatment tool according claim 10, further comprising a first protrusion disposed at one of the fixed handle and the movable handle, wherein the first protrusion extends from a surface of the one of the fixed handle and the movable handle toward the other handle and the first protrusion is configured to contact the other handle when the movable handle is moved toward to the fixed handle, and wherein an amount of a stroke of the movable handle is adjustable by at least one of (i) adjusting an amount the first protrusion extends from the surface of the one of the fixed handle and the movable handle and (ii) adjusting a location of the first protrusion on the one of the fixed handle and the movable handle in a longitudinal direction of the one of the fixed handle and the movable handle.

15. A manufacturing method of the treatment tool according to claim 10, comprising:

measuring an amount of a gripping force between the treatment portion and the jaw when the fixed handle and the movable handle are gripped; and adjusting the amount of the gripping force to a specific amount by adjusting the rigidity of the one or more of the movable handle and the jaw.

16. The treatment tool according claim 10, wherein the one or more of the movable handle and the jaw has an insertion hole, and wherein the second adjusting member is disposed into the insertion hole.

17. The treatment tool according claim 10, further comprising:

a shaft extended from the fixed handle in a longitudinal direction, wherein the treatment portion projects distally from a distal end of the shaft, the treatment portion is configured to treat a living tissue between the jaw and the treatment portion by ultrasonic vibration, wherein the jaw is configured to rotate to hold the living tissue between the jaw and the treatment portion, and wherein the movable handle is extended from the jaw in a proximal direction, the movable handle configured to move relative to the fixed handle between a furthest position and a closest position defining a stroke of the movable handle and so as to move the jaw to open or close against the treatment portion.

18. The treatment tool according claim 10, wherein the second adjusting member is configured to:

change a threaded state against the one or more of the movable handle and the jaw, and advance and retract against the one or more of the movable handle and the jaw along a longitudinal direction of the one or more of the movable handle and the jaw to adjust the rigidity of the one or more of the movable handle and the jaw.

19. The treatment tool according claim 10, wherein the second adjusting member is disposed inside the jaw.

* * * * *